(12) United States Patent
Cisar et al.

(10) Patent No.: US 7,329,400 B2
(45) Date of Patent: Feb. 12, 2008

(54) GENERATOR FOR RHENIUM-188

(75) Inventors: Alan Cisar, Cypress, TX (US); Todd Adams, Franklin, TX (US); Paul Sylvester, Waltham, MA (US)

(73) Assignee: Lynntech, Inc., College Station, TX (US)

( * ) Notice: Subject to any disclaimer, the term of this patent is extended or adjusted under 35 U.S.C. 154(b) by 1152 days.

(21) Appl. No.: 10/175,515

(22) Filed: Jun. 19, 2002

(65) Prior Publication Data

US 2003/0235530 A1    Dec. 25, 2003

(51) Int. Cl.
*A61K 51/00* (2006.01)
*A61M 36/14* (2006.01)

(52) U.S. Cl. .................. 424/1.49; 424/1.11; 424/1.37; 424/1.61; 424/9.1

(58) Field of Classification Search ............... 424/1.11, 424/1.61, 1.37, 1.65, 1.49, 9.1; 534/10
See application file for complete search history.

(56) References Cited

U.S. PATENT DOCUMENTS

| | | |
|---|---|---|
| 4,159,311 A | 6/1979 | Lee et al. |
| 4,326,961 A | 4/1982 | Lee et al. |
| 4,392,961 A | 7/1983 | Lee et al. |
| 4,392,979 A | 7/1983 | Lee et al. |
| 4,392,980 A | 7/1983 | Lee et al. |
| 4,642,193 A | 2/1987 | Miyata et al. |
| 4,727,167 A | 2/1988 | Burba, III et al. |
| 4,812,245 A | 3/1989 | Burba, III et al. |
| 4,859,431 A | 8/1989 | Ehrhardt |
| 5,186,913 A | 2/1993 | Knapp, Jr. et al. |
| 5,729,821 A | 3/1998 | Knapp et al. |
| 6,280,693 B1 | 8/2001 | Bauman et al. |

FOREIGN PATENT DOCUMENTS

GB    2 067 343 A    7/1981

OTHER PUBLICATIONS

Kovanda et al, Solid State Sciences, 5, (2002), 1019-1026.*
Q. Liang, G. J. Ehrhardt, A.R. Ketring and R. Miller, *Radiochim. Acta*, "Effect of Stoichiometric and Preparation Parameters on W-188/Re-188 Gel Generator Performance", 79(2), 137-140, 1997.
A.F. Novgorodov, F. Bruchertseifer, J. Brockmann, N. A. Lebedev, and F. Rosch, *Radiochim. Acta*, Thermochromatographic Separation of No-Carrier-Added Re-186 or Re-188 from Tungsten Targets Relevant to Nuclear Medical Applications, 88(3-4), 163-167, 2000.
Q Liang, G. J. Ehrhardt, A. R. Ketring and R. Miller, Effect of Stoichiometric and Preparation Parameters on W-188/Re-188 Gel Generator Performance, 1997, 137-140.
A. F. Novgorodov, F. Brucherseifer, J. Brockmann, N. A. Lededev, and F. Rösch, Thermochromatographic separation of no-carrier-added $^{186}$Re from tungsten targets relevant to nuclear medical applications, Feb. 22, 2000, 163-167.
M. Khalid, A. Mushtaq, and M. Z. Iqbal, sorption of Tungsteen (VI) and Rhenium (VII) on Various Ion-Exchange Materials, © 2000, 283-294.
International Search Report; International application No. PCT/US 03/19105; International Filing Date Jun. 18, 2003; 4 pages.
J. Serrano, V. Bertin, and S. Bulbulian; "$^{99}$Mo Sorption by Termally Treated Hydrotalcites"; Langymuir, 2000, vol. 16, pp. 3355-3360.
Abstract XP002260841, 1982.
Abstract XP-002260840, 1991.

* cited by examiner

*Primary Examiner*—Dameron L. Jones
(74) *Attorney, Agent, or Firm*—Jeffrey L. Streets; Streets & Steele

(57) ABSTRACT

Radioisotope generators comprising inorganic layered hydroxide composition, such as magnesium aluminates and lithium aluminates. These inorganic layered hydroxides form anion exchange materials that exhibit surprisingly high selective affinities for certain radioisotopes. Inorganic layered hydroxides have been prepared and shown to have high affinity for tungstate anions, the anion form of tungsten-188, yet low affinity for perrhenate anions, the anion form of rhenium-188.

53 Claims, No Drawings

GENERATOR FOR RHENIUM-188

BACKGROUND OF THE INVENTION

1. Field of the Invention

A generator that may be loaded with a parent isotope, which is retained on the generator and readily releases the daughter isotope formed by the decay of the parent and methods of use and construction thereof.

2. Background of the Related Art

Rhenium-188 ($^{188}$Re, an isotope of rhenium having 75 protons and 113 neutrons in its nucleas) is chemically very similar to the well known and widely utilized isotope technetium-99m ($^{99m}$Tc), but while $^{99m}$Tc is a gamma ray ($\gamma$) emitter that is useful for single photon emission computed tomography (SPECT) imaging, $^{188}$Re is a beta emitter ($\beta^-$) producing a 2.12 MeV electron as it decays to stable $^{188}$Os. This high energy beta emission and short half life (16.9 hours) makes $^{188}$Re an excellent isotope for radiotherapeutic applications. $^{90}$Y, an isotope with a similar beta emission (2.28 MeV) already has FDA approval for the treatment of various cancers (e.g., non-Hodgkin's lymphoma) and it is anticipated that $^{188}$Re can be used in a similar role and open up access to additional coordinating groups and antibodies.

$^{90}$Y has a half life of approximately 64 hours which means that it can be produced at a central location and distributed to clinics and research establishments. However, $^{188}$Re has a half life of only 16.9 hours which is too short for the isotope to be conveniently shipped, and thus means that it must be generated at the site of use. As a consequence, the development of a commercial, reliable generator is essential to ensure that the clinical possibilities of this isotope are fully realized. This short half-life also means that the activity of the isotope rapidly dies away, reducing the chance for damage to other areas of the body if the targeting agent to which the isotope has been attached breaks down, releasing the isotope into other areas of the body where it isn't desired.

Knapp describes a $^{188}$Re generator having a dual column system that retains a $^{188}$W "cow" on a chromatographic alumina column. The $^{188}$Re is eluted using a saline solution, and the saline solution converted to the pure perrhenic acid by a subsequent ion exchange using a cation exchange column. This is at best a two step process, with the potential for yield loss in the ion exchange step. Alumina is a poor ion exchange material with a low ion exchange capacity, poor selectivity, and limited stability. This may lead to premature column blocking and the release of aluminum, or even the parent $^{188}$W, into the $^{188}$Re product.

A "one pot" synthesis has been developed for a gel type generator, with the cow retained on a gel column produced by dissolving the target under carefully controlled conditions. This method is described as applicable to both $^{188}$Re/$^{188}$W and $^{99m}$Tc/$^{99}$Mo. The method has a limitation in that the start of $^{188}$W breakthrough occurs after only 5 to 10 elutions, far too few for a practical generator.

A gas phase method has been described for separating $^{188}$Re from $^{188}$W based on the volatility of HReO$_4$. In this approach, described as thermochromatographic separation, the irradiated $^{186}$W target is heated to ~1,000° C. to volatilize the Re containing species, which is carried to a colder region in a stream of moist air. The advantage of this method is that the $^{186}$W enriched target can be reused. The disadvantage is that the high temperatures required by this process can potentially volatilize other, less desirable materials out of the target as well. The extreme conditions required also means that this method is clearly unsuitable for the on site production of $^{188}$Re, which is essential given the short half life.

Khalid et al. published a study in which they examined a variety of materials with the potential of serving as the support for the $^{188}$W cow in a $^{188}$Re generator. They examined both organic and inorganic materials including charcoal, silica-gel, alumina, lead, a number of transition metal oxides, and conventional ion exchange resins. None of these materials were found to be very effective at sequestering $^{188}$W. In most cases the tungsten and rhenium affinities were only a factor of 10 to 100 different, inadequate for achieving a good separation. The best results reported were achieved at low pH, complicating the use of the perrhenate in complexation processes.

Most of the well known inorganic ion exchange materials, such as zeolites, titanium phosphates, and zirconium phosphates, are cation exchangers. Only a few materials are known that are anion exchangers, but an anion exchanger is required to sequester tungsten-188 because in aqueous systems the stable form of tungsten is the tungstate anion ($WO_4^=$) or its anionic derivatives.

Most inorganic materials used as anion exchangers can be generally classed as hydrous metal oxides (e.g., alumina, zirconia, etc.). These materials can be considered to consist of discrete metal oxide clusters covered by surface hydroxyl groups. At low pH, these hydroxide groups become protonated and the material develops a positive charge. Anions are thus absorbed to maintain electroneutrality. At high pH, the hydroxyl groups lose protons and the material becomes negatively charged and acts as a cation exchanger. Thus, this class of materials are effectively amphoteric and can be either anion or cation exchangers, depending upon the pH. Another disadvantage of these materials is that they are poorly characterized and almost impossible to reproducibly synthesize making them poor candidates for use in a system producing isotopes for the treatment of human patients. Radiation stability is also an issue and physical breakdown of the material can cause problems in generator operation.

Therefore, there is a need for improved methods, apparatuses, and compositions for separating rhenium-188 from its parent tungsten-188. It would be desirable if the compositions were highly radiation resistant, thermally stable, chemically stable, and non-toxic. It would be even more desirable if the compositions and methods provided very high affinities for the parent as opposed to the daughter isotope.

SUMMARY OF THE INVENTION

The present invention provides a rhenium-188 generator comprising an elutable container defining an eluant flow path, the container containing a matrix comprising a substantially non-elutable inorganic layered hydroxide compound containing tungsten-188. The inorganic layered hydroxide composition may comprise a hydrotalcite anion exchange material, such as a magnesium aluminate prepared by reacting aluminum hydroxide with magnesium chloride, or a lithium aluminate prepared by reacting lithium salt with hydrous alumina. Tungsten-188 is provided in the form of a tungstate anion, preferably exchanged onto the inorganic layered hydroxide from a sodium tungstate solution at a pH between 6.5 and 7.

The invention also provides a radionuclide generator for producing rhenium-188 comprising an insoluble inorganic layered hydroxide matrix including a tungstate compound containing tungsten-188, the matrix being permeable to fluid passage and permitting diffusion of rhenium-188 therethrough. The matrix is preferably prepared by reacting aluminum hydroxide with magnesium chloride to form a magnesium aluminate. The preferred magnesium aluminate has a magnesium to aluminum ratio of between about 0.5 and about 2. Alternatively, the matrix may be prepared by reacting lithium salt with hydrous alumina to form a lithium aluminate.

The present invention further provides a process for preparing a radionuclide generator useful for producing a solution containing rhenium-188, comprising: disposing a substantially non-elutable inorganic layered hydroxide anion exchange composition into a container defining an eluant flow path; and exchanging tungstate anions onto the anion exchange composition. The anion exchange composition is preferably a magnesium aluminate or a lithium aluminate. The tungstate anions are preferably provided by a sodium tungstate solution, most preferably at a pH between 6.5 and 7. It is also preferred that the tungstate anions exchange with up to 10% of the theoretical anion exchange capacity of the anion exchange composition.

The present invention additionally provides a process for preparing a perrhenate solution, comprising eluting perrhenate from a matrix consisting essentially of an insoluble inorganic layered hydroxide containing tungstate anions. One suitable inorganic layered hydroxide is prepared by reacting aluminum hydroxide with magnesium chloride to form the insoluble inorganic layered hydroxide and loading the insoluble inorganic layered hydroxide with tungstate anions. Optionally, the step of loading further comprises forming an aqueous slurry of the insoluble inorganic layered hydroxide and adding sodium tungstate to the slurry. The insoluble inorganic layered hydroxide is then separated from the slurry. The step of eluting is performed with an eluant solution, preferably an aqueous solution having a substantially neutral pH and a small concentraion of a salt appropriate for the final application.

The insoluble inorganic layered hydroxides of the invention comprises a mixture of at least two cations with surrounding shells of bound hydroxyl groups, for example magnesium aluminate and lithium aluminate. These insoluble inorganic layered hydroxides of the invention have exhibited a tungstate distribution factor greater than 15,000 milliliters/gram. Optionally, the perrhenate may be purified by passing the perrhenate through a secondary matrix capable of adsorbing any tungstate in solution. Furthermore, the perrhenate may be concentrated in a secondary anion exchange column; and eluted from the anion-exchange column with a saline solution. Preferably, the perrhenate is eluted as a solution having a volume between 0.5 and 50 milliliters and containing greater than 10 millicuries of rhenium-188. The perrhenate ($ReO_4^-$) solutions may be used in various manners, including obtaining rhenium-188 from the perrhenate and conjugating the rhenium-188 to an antibody, such as an antibody that recognizes tumor-associated antigens.

DETAILED DESCRIPTION OF THE INVENTION

The present invention provides certain radioisotope generators from inorganic layered hydroxides. The inventors have discovered that, under appropriate conditions, certain inorganic layered hydroxides exhibit surprisingly high selective affinities for certain radioisotopes. In accordance with the present invention, inorganic layered hydroxides have been prepared and shown to have high affinity for tungstate anions, the oxo anion form of tungsten-188, yet low affinity for perrhenate anions, the oxo anion form of rhenium-188.

The inorganic layered hydroxides of the present invention may have a variety of compositions, but they are generally referred to as magnesium aluminates and lithium aluminates. In general, the magnesium aluminates are precipitated as the product of a reaction between highly dispersed amorphous aluminum hydroxide and a solution of magnesium chloride at a controlled pH to yield an insoluble microcrystalline layered product with both magnesium and aluminum randomly distributed throughout the crystal structure. These magnesium aluminates may be described by the formula $(Mg_{(2-n)}Al_n(OH)_4Z_n*mH_2O$, where Z is a negative valence ion (anion), n has a value of from about 0.2 to 1.5; and m being a value of zero or more. The preparation of magnesium aluminates is described in U.S. Pat. No. 4,326,961, which patent is incorporated by reference herein.

Magnesium aluminates are similar to brucite, except that a portion of the magnesium atoms are substituted with aluminum atoms. Aluminum atoms have a similar ion radii to magnesium, but aluminum has a positive valence of three instead of magnesium's positive valence of two. Consequently, the aluminum to magnesium ratio, or the extent to which aluminum is substituted into the composition, determines the anion exchange capacity of the composition.

In general, lithium aluminates are prepared by reacting lithium salts with hydrous alumina to form $(LiA_x)_y*2Al(OH)_3*nH_2O$, where: A represents one or more anions and/or negative-valence radicals, including mixtures of such anions and/or negative-valence radicals, where the anions and negative-valence radicals may be monovalent or multivalent; x represents a quantity of A ions and/or radicals sufficient to substantially satisfy the valence requirements of the Li; n represents the number of waters of hydration, and may be zero or more, especially about 0 to about 6; and y is a numerical value sufficient to maintain the crystalline structure, especially about 0.5 to about 2. These compositions and methods of forming these compositions are described in U.S. Pat. No. 4,727,167, which patent is incorporated by reference herein.

Lithium aluminates are similar to gibbsite or bayerite, except that a portion of the octahedral holes in the $Al(OH)_3$ sheets are filled with lithium cations. The lithium cations provide the otherwise neutral composition with a positive charge that makes the composition suitable for anion exchange. Consequently, the amount of lithium exchanged into the composition determines the anion exchange capacity of the composition.

After carrying out the foregoing reactions to form an inorganic layered hydroxide, the precipitate is washed with DI water to remove all unreacted, and therefore soluble material. The precipitate is then converted to the tungstate form by ion exchanging with a tungstate solution, such as a solution of sodium tungstate ($Na_2WO_4$), preferably at a pH of between about 6.5 and about 7.

The inorganic layered hydroxides formed in accordance with the invention exhibit good thermal stability and good radiation stability.

EXAMPLE 1

Determination of the Tungsten Affinity of Candidate Compounds

Two factors are important in the ion exchange chemistry of a material that is to be used as the support material for a radioisotope generator. The material must have a very high affinity for the parent isotope, tungsten in this case, and must have a low affinity for the daughter.

A series of synthetic hydrotalcites were produced according to the procedure described in Lee and Bauman, U.S. Pat. No. 4,326,961, which patent is incorporated by reference herein. This procedure is based on the precipitation of highly dispersed amorphous aluminum hydroxide that is reacted with a solution of magnesium chloride at a controlled pH to yield an insoluble microcrystalline layered product with both magnesium and aluminum apparently randomly distributed throughout the crystal structure.

After thoroughly washing with DI water to remove all unreacted, and therefore soluble material, the white precipitate was converted to the tungstate form by ion exchanging with a solution of sodium tungstate ($Na_2WO_4$). In each case the amount of sodium tungstate used was equivalent to 10% of the calculated anion exchange capacity of the specimen. To carryout the exchange the magnesium aluminate was slurried in DI water and the pH adjusted to between 6.7 and 7 using dilute HCl. Sodium tungstate was dissolved in DI water and added the slurry. The mixture was stirred for several hours with the pH monitored and adjusted using HCl to keep it between 6.5 and 7.

The magnesium aluminate was separated from the solution by centrifugation and the amount of tungstate remaining in solution determined by atomic absorption spectroscopy (AA). In all cases, no tungsten was detected in the supernatant, indicating a very high affinity of the materials for the tungstate anion.

This data was used to estimate the resin's affinity for the anion as a distribution coefficient ($K_d$) using the equation:

$$K_d = \frac{C_i - C_0}{C_0} * \frac{V}{M}$$

where:
 $C_0$ is the concentrations of the anion in solution after mixing with the ion exchange material,
 $C_i$ is the concentrations of the anion before mixing with the ion exchange material,
 V is the volume of the solution containing the anion in mL, and
 M is the mass of ion exchanger in g.

The $K_d$ values in Table I represent the minimum values for each compound. They were determined by assuming that the final tungsten concentration was equal to the detection limit by the technique used (atomic absorption spectroscopy). The actual concentrations could have been substantially less.

TABLE I

Preliminary Determination of Tungsten Affinity

| Mg | Al | $K_d$ (mL/g) |
|---|---|---|
| 1 | 1.5 | 15,100 |
| 1 | 1 | 13,300 |
| 2 | 1 | 8,350 |
| 3 | 1 | 6,550 |

Since the theoretical anion exchange capacity increases with aluminum content, the more aluminum-rich materials were equilibrated with higher concentrations of tungstate. Because the same final concentration (the minimum detection limit of tungsten by AA, 0.2 ppm) was used in all cases, this gives the impression that the higher aluminum contents lead to a higher $K_d$ values. In actuality the values shown in Table I represent the minimum $K_d$ values. Because the actual tungstate concentration remaining in solution may have been over an order of magnitude below the values used here, and therefore the actual $K_d$ values are definitely larger, and possibly much larger. All of these unoptimized $K_d$ values are larger than the best values reported elsewhere, in addition, these values were obtained at neutral pH, which is better for forming complexes with antibody carriers that the low (<3) pH conditions used by previous workers.

EXAMPLE 2

Determine the Tungsten Affinity of a Comparative Example

Chromatographic alumina, a standard support for $WO_4^=$, has a $K_d$ of 44 when prepared and tested following the same procedure as described in Example 1. This corresponds to absorbing less than half of the tungstate initially in solution.

EXAMPLE 3

Demonstrate that Tungsten is Effectively Retained on the Ion Exchanger

After completing the analysis described in Example 1, the tungstate loaded magnesium aluminate specimens were washed several times with DI water to simulate the elution of product from a generator. They were then dissolved to determine how much tungsten remained on the hydrotalcite. This was accomplished by slurrying the tungstate loaded aluminate in DI water and adjusting the pH to 2.5. (Higher acidities would have accelerated the dissolution of the hydrotalcite, but at pH values below 1.0 tungstate precipitates as tungstic acid, $H_2WO_4$). The mixture was stirred for several hours at 80° C. with the pH adjusted as needed. The resulting solution was analyzed for tungsten. The subsequent analysis indicated that tungsten initially absorbed into the aluminate remained there.

EXAMPLE 4

Demonstrate the Amount of Tungsten Retained on Alumina

The alumina prepared and examined in Example 2 was treated and analyzed in the same manner as described in Example 3. The analysis showed that little tungstate was retained after washing with DI water.

EXAMPLE 5

Determine the Rhenium Affinity of Candidate Compounds.

Clearly the magnesium aluminum hydrotalcite has excellent retention properties for tungstate, but safely keeping the [188]W cow out of solution is only one of the factors needed for an effective isotope generator. It is also necessary that the desired daughter, which is generally present at much lower concentrations, can be readily eluted. To evaluate these properties we utilized a perrhenate analog, pertechnetate ($TcO_4^-$), as a radiotracer. In these experiments 0.4-0.5 g of magnesium aluminate was dispersed in a 0.9% saline solution containing 2.94 μCi/mL of $^{99}$Tc (half-life $2.1 \times 10^5$ y) and shaken for two hours. The mixture was then centrifuged to separate the solid from the solution and the solution analyzed by liquid scintillation counting to determine the amount of $^{99}$Tc remaining in solution.

The results, shown in Table II, clearly demonstrate that all of these compounds have very low affinities for pertechnetate. On average, 9% of the pertechnetate was absorbed by the anion exchanger, an amount that can be accounted for by the amount of solution required to wet the solids that were separated out. Since perrhenate and pertechnetate behave almost identically in aqueous solution (from an anion exchange perspective), it can safely be assumed that the hydrotalcites tested here will also have a low affinity for perrhenate.

TABLE II

Preliminary Determination of Pertechnetate Affinity

| Mg | Al | $^{99}$Tc (in solution) | $K_d$ |
|---|---|---|---|
| 1 | 1.5 | 97.2% | 1.4 |
| 1 | 1 | 89.4% | 4.6 |
| 2 | 1 | 85.8% | 4.0 |
| 3 | 1 | 91.1% | 2.9 |

While the foregoing is directed to the preferred embodiment of the present invention, other and further embodiments of the invention may be devised without departing from the basic scope thereof, and the scope thereof is determined by the claims that follow.

What is claimed is:

1. A rhenium-188 generator comprising an elutable container defining an eluant flow path, the container containing a matrix comprising a substantially non-elutable inorganic layered hydroxide compound containing tungsten-188.

2. The generator of claim 1, wherein the inorganic layered hydroxide composition comprises hydrotalcite structured anion exchange material.

3. The generator of claim 2, wherein the hydrotalcite structured material comprises a magnesium aluminate.

4. The generator of claim 3, wherein the hydrotalcite is prepared by reacting aluminum hydroxide with a magnesium salt.

5. The generator of claim 4, wherein the magnesium salt is magnesium chloride.

6. The generator of claim 1, wherein the inorganic layered hydroxide composition comprises a lithium aluminate.

7. The generator of claim 6, wherein the lithium aluminate is prepared by reacting a lithium salt wit hydrous alumina.

8. The generator of claim 1, wherein the tungsten-188 is provided in the form of a tungstate anion.

9. The generator of claim 3, wherein the tungsten-188 is provided in the form of a tungstate anion.

10. The generator of claim 6, wherein the tungsten-188 is provided in the form of a tungstate anion.

11. The generator of claim 8, wherein the tungstate anion is exchanged onto the inorganic layered hydroxide at a pH between 6.5 and 7.

12. The generator of claim 10, wherein the tungstate anion is provided as a sodium tungstate solution.

13. A radionuclide generator for producing rhenium-188 comprising an insoluble inorganic layered hydroxide matrix including a tungstate compound containing tungsten-188, the matrix being permeable to fluid passage and permitting diffusion of rhenium-188 therethrough.

14. The radionuclide generator of claim 13, wherein the matrix is prepared by reacting aluminum hydroxide with magnesium chloride.

15. The radionuclide generator of claim 13, wherein the matrix has a hydrotalcite structure.

16. The radionuclide generator of claim 15, wherein the hydratalcite structured compound has a magnesium to aluminum ratio of between about 0.5 and about 2.

17. The generator of claim 13, wherein the matrix is prepared by reacting lithium salt with hydrous alumina.

18. The generator of claim 13, wherein the matrix comprises a lithium aluminate.

19. A process for preparing a radionuclide generator useful for producing a solution containing rhenium-188, comprising:
  disposing a substantially non-elutable inorganic layered hydroxide anion exchange composition into a container defining an eluant flow path; and
  exchanging tungstate anions onto the anion exchange composition.

20. The process of claim 19, wherein the anion exchange composition is a magnesium aluminate.

21. The process of claim 19, wherein the anion exchange composition is a lithium aluminate.

22. The process of claim 19, further comprising:
  reacting aluminum hydroxide with a magnesium salt to form the anion exchange composition.

23. The process of claim 22 where the magnesium salt is magnesium chloride.

24. The process of claim 17, wherein the tungstate anions are provided by a sodium tungstate solution.

25. The process of claim 20, wherein the tungstate anions are provided by a sodium tungstate solution.

26. The process of claim 19, wherein the step of exchanging is performed at a pH between 6.5 and 7.

27. The process of claim 19, wherein the tungstate anions exchange with up to 10% of the theoretical anion exchange capacity of the anion exchange composition.

28. A process for preparing a perrhenate solution, comprising:
  eluting perrhenate from a matrix consisting essentially of an insoluble inorganic layered hydroxide in the tungstate form.

29. The process of claim 28, wherein the inorganic layered hydroxide comprises a combination of cations selected from magnesium/aluminum, lithium/aluminum, and magnesium/lithium.

30. The process of claim 28, further comprising:
  reacting aluminum hydroxide with a magnesium salt to form the insoluble inorganic layered hydroxide; and
  loading the insoluble inorganic layered hydroxide with tungstate anions.

31. The process of claim 30 where the magnesium salt is magnesium chloride.

32. The process of claim 30, wherein the step of loading further comprises:
  forming an aqueous slurry of the insoluble inorganic layered hydroxide; and
  adding sodium tungstate to the slurry.

33. The process of claim 32, further comprising:
  agitating the slurry.

34. The process of claim 32, further comprising:
  maintaining the pH of the slurry between 6.5 and 7.

35. The process of claim 32, further comprising:
separating the insoluble inorganic layered hydroxide from the slurry.

36. The process of claim 28, wherein the step of eluting is performed with an eluant that is an aqueous solution.

37. The process of claim 28, wherein the step of eluting is performed with an eluant solution including a salt.

38. The process of claim 28, wherein the step of eluting is performed with an eluant having neutral pH.

39. The process of claim 28, wherein the perrhenate solution has a radiochemical purity of greater than 99%.

40. The process of claim 28, wherein the insoluble inorganic layered hydroxide exhibits a tungstate distribution factor greater-tan 1,000 milliliters/gram.

41. The process of claim 28, wherein the insoluble inorganic layered hydroxide exhibits a tungstate distribution factor greater than 5,000 milliliters/gram.

42. The process of claim 28, wherein the insoluble inorganic layered hydroxide exhibits a tungstate distribution factor greater than 10,000 milliliters/gram.

43. The process of claim 28, wherein the insoluble inorganic layered hydroxide exhibits a tungstate distribution factor greater than 15,000 milliliters/gram.

44. The process of claim 28, further comprising:
purifying the perrhenate by passing the perrhenate trough a secondary matrix capable of adsorbing tungsten.

45. The process of claim 28, further comprising:
obtaining rhenium-188 from the perrhenate; and
conjugating the rhenium-188 to an antibody.

46. The process of claim 28, further comprising:
obtaining rhenium-188 from the perrhenate; and
conjugating the rhenium-188 to an antibody that recognizes tumor-associated antigens.

47. The process of claim 28, wherein the elated perrhenate has the formula ($ReO_4$).

48. The process of claim 28, wherein the perrhenate is formed by radioactive decay of the tungstate.

49. The process of claim 28, wherein the eluted perrhenate is in the form of sodium perrhenate ($Na^+ReO_4$).

50. The process of claim 28, further comprising:
concentrating the perrhenate in a secondary anion exchange column; and
eluting the concentrated perrhenate from the anion-exchange column with a saline solution.

51. The process of claim 28, characterized in that the perrhenate is eluted as a solution having a volume between 0.5 and 50 milliliters and containing greater than 10 millicuries of rhenium-188.

52. The process of claim 28, wherein the inorganic layered hydroxide comprises a mixture of at least two cations with surrounding shells of bound hydroxyl groups.

53. The process of claim 28, where the inorganic layered hydroxide is selected from magnesium aluminate and lithium aluminate.

* * * * *

UNITED STATES PATENT AND TRADEMARK OFFICE
CERTIFICATE OF CORRECTION

PATENT NO. : 7,329,400 B2  Page 1 of 1
APPLICATION NO. : 10/175515
DATED : February 12, 2008
INVENTOR(S) : Alan Cisar, Todd Adams and Paul Sylvester It is certified that error appears in the above-identified patent and that said Letters Patent is hereby corrected as shown below:

Column 1, after the Title insert the following:

--STATEMENT REGARDING FEDERALLY SPONSORED RESEARCH OR DEVELOPMENT

This invention was made with government support under grants 1 R43 CA97626-01 and 5 R44 CA097626-03 awarded by NIH. The government has certain rights in this invention.--

Signed and Sealed this

Thirteenth Day of May, 2008

JON W. DUDAS
*Director of the United States Patent and Trademark Office*